United States Patent [19]

Lauro et al.

[11] Patent Number: 4,872,188
[45] Date of Patent: Oct. 3, 1989

[54] REGISTRATION CORRECTION FOR RADIOGRAPHIC SCANNERS WITH SANDWICH DETECTORS

[75] Inventors: Karen L. Lauro, Euclid; Richard A. Sones, Cleveland Hts, both of Ohio

[73] Assignee: Picker International, Inc., Highland Hts., Ohio

[21] Appl. No.: 126,165

[22] Filed: Nov. 27, 1987

[51] Int. Cl.[4] ............................................. G01N 23/04
[52] U.S. Cl. ....................................... 378/62; 378/18; 378/98
[58] Field of Search .................... 378/5, 18, 19, 62, 98, 378/99, 205, 207; 358/111; 250/252.1

[56] References Cited

U.S. PATENT DOCUMENTS

| Re. 32,164 | 5/1986 | Kruger | 378/19 |
|---|---|---|---|
| 4,029,963 | 6/1977 | Alvarez et al. | 378/5 |
| 4,366,574 | 12/1982 | Hill | 378/99 |
| 4,419,577 | 12/1983 | Cuth | 378/207 |
| 4,511,799 | 4/1985 | Bjorkholm | 378/5 |
| 4,517,460 | 5/1985 | Meulenbrugge et al. | 378/207 |
| 4,626,688 | 12/1986 | Barnes | 250/361 |
| 4,709,382 | 11/1987 | Sones | 328/62 |
| 4,780,897 | 10/1988 | McDaniel et al. | 378/5 |

OTHER PUBLICATIONS

"Generalized Image Combinations in dual KVP Digital Radiography" by Lehmann, et al., Med. Phys. 8(5), Sep./Oct. 1981, pp. 659–667.
"Digital Radiography of the Chest: Clinical Experience with a Prototype Unit" by Fraser, et al., Radiology, 148, Jul. 1983, pp. 1–5.
"Digital Radiography of the Chest: Design Features and Considerations for a Prototype Unit" by Tesic, et al., Radiology 148, Jul. 1983, pp. 259–264.

Digital Processing, 2nd ed. vol. 2, Rosenfeld and Kak, pp. 22–37.
"Digital Image Processing" by W. Pratt, John Wiley and Sons, pp. 562–567.
"Digal Chest Radiography: Performance Evaluation of a Prototype Unit" by Barnes, et al., Radiology, vol. 154, No. 3, p. 801–806, Mar. 1985.
"Single Slit Digital Radiography" by Tesic, et al., AJR 142:697–702, Apr. 1984.
"Detector for Dual Energy Digital Radiography" by Barnes, et al., Radiology, 156:537–540, 1985.

Primary Examiner—Carolyn E. Fields
Assistant Examiner—David P. Porta
Attorney, Agent, or Firm—Fay, Sharpe, Beall, Fagan, Minnich & McKee

[57] ABSTRACT

A fan beam of radiation (12) is projected on first and second detector arrays (18, 20). The detector arrays and fan beam are swept across a phantom (D). Fine wires (82) in the phantom each cast shadows over fractions of a plurality of the detectors during the sweep. Phantom images (44, 46) are generated from the first and second detector arrays with corresponding pixels of each image corresponding to the same path between a radiation source (10) and corresponding detectors in the arrays. A linear interpolation (50) interpolates the pixels of one of the images to shift their effective spatial position. A transform means (52) transforms the linear interpolated and second phantom image into at least one composite image (54). The linear interpolation is iteratively adjusted (C) to minimize phase change artifacts in corresponding pixels of the composite image. After the appropriate interpolation for each detector or group of detectors has been determined, the appropriate linear interpolations are stored (72). Thereafter, the stored linear interpolations are utilized each time a subject is examined.

23 Claims, 3 Drawing Sheets

REGISTRATION CORRECTION FOR RADIOGRAPHIC SCANNERS WITH SANDWICH DETECTORS

BACKGROUND OF THE INVENTION

This invention relates to the art of diagnostic imaging. It finds particular application in conjunction with dual energy, scanned detector array medical diagnostic digital radiography, and will be described with particular reference thereto. However, it is to be appreciated that the invention may find further application in conjunction with other imaging techniques such as single or multiple energy digital radiography, computed tomography, and the like.

In prior art digital radiography, each image is commonly a rectangular array of pixels. The pixel value, which is usually displayed as gray scale, is indicative of the degree of radiation attenuation or transmissivity through a corresponding path of the region of interest.

By conducting the same examination with two different energy levels, material specific images, called basis images, can be derived, in addition to a normal image which a linear combination of high and low energy images. With human patients, soft tissue and calcium specific images are most commonly generated.

It is to be appreciated that the accuracy of the basis images is dependent upon the degree to which they are determined from high and low energy radiation beams that have passed through the same tissue. When the high and low energy data has been collected serially, i.e. high energy data was collected followed by low energy data, registration of the two images is difficult. Patient motion between the images complicates the registration procedure and, in some cases, makes it impossible. Compensation can sometimes be made for simple, lateral patient movement by registering portions of the image data separately. A detector is defined as a phosphor screen, photodiode pair. Movement of the patient toward or away from the detector causes magnification errors.

To avoid patient movement problems, the high and low energy data can be collected concurrently. However, difficulty still arises in aligning the high and low energy detectors precisely. Sometimes, high and low energy detectors are separated by a filter such that lower energy radiation causes light emission primarily from the front phosphor and high energy radiation causes light emission from the rear phosphor. A first array of photodiodes or other photodetectors are disposed along the front phosphor screen and a second array of photodiodes or other radiation detectors are mounted to the rear phosphor screen. Commonly, photodiode chips or modules are manufactured with a plurality of photodiodes in a linear array, e.g. 32 photodiodes. A plurality of the arrays or modules are abutted and aligned until the entire examination region is spanned.

The phosphor screens are commonly arced such that all points along the screen are equidistant from the radiation source. Aligning the front and back photodiode arrays is rendered more difficult by the curvature of the phosphor screens. The front and back detectors tend to magnify the spatial position to different degrees. In some scanners, the thickness of the phosphor screens and the filter create a parallax problem in the alignment of the front and back diode arrays.

Mechanical alignment techniques provide relatively good alignment between the corresponding high and low energy photodiode arrays. Basis images are derived by a non-linear function of the high and low image values. Therefore misalignments of even a small fraction cause significant errors at a material boundary. The sign of the error depends on the direction of misalignment and direction of a change in material thickness. At abrupt material changes, both positive and negative errors occur in close proximity. These artifacts are commonly called phase change errors. The non-linear basis transformation that separates high and low energy data into material specific images exaggerates the phase change errors and the resultant artifacts in the material specific images. Because the photodiodes are commonly very small, e.g. on the order of one millimeter, even misalignments as little as a tenth of a millimeter or less cause significant errors in the basis images.

Analogous registration problems occur when a multilinear array of detectors is scanned. A multilinear detector array is made up of a plurality of multilinear chips abutted together forming an array of detector elements. Each chip is a 20 photodiode array composed of m columns x n rows of active elements which are integrated over time to produce signals effectively equivalent to a linear array of n elements. The detectors in each row sequentially shift or move into alignment with each pixel location. Each detector is sampled when in alignment with the pixel. The sampled data is summed with data from other detectors in the row sampled when each was in alignment with the same pixel. An example of a multilinear detector array utilizes the shift and add sequence can be found in Kruger U.S. Pat. No. Re. 32,164 which is incorporated herein by reference. It is to be appreciated that if the detectors in the row are not perfectly aligned, the data sampled from each will not represent radiation that has traversed the same path through the patient. Any misalignment of the sequential sampled detectors again causes image degradation.

In a single linear array detector system, the detectors are commonly wider than one pixel. Pre-patient collimation assures that the effective detector width is constant along the array. In one prior art alignment technique, two sequentially collected images are brought into alignment using translation and rotation. Patient movement may require different areas of the images to have different translational or rotational differences.

In accordance with the present invention, a new and improved electronic data processing technique is provided for correcting basis images for high and low energy photodiode pair misalignment.

SUMMARY OF THE INVENTION

In accordance with one aspect of the present invention, a radiographic apparatus is provided. The source of radiation projects a radiation beam through a region of interest or examination region which is adapted to receive a subject to be examined. A first array of radiation detectors and a second array of radiation detectors are each sampled in alignment with the radiation source and the same plane through an examination region. The radiation detectors of the first and second arrays produce radiation attenuation data. A transform means receives the attenuation data from the radiation detectors and derives at least one image therefrom. A registration adjustment means adjusts the signals from at least one of the first and second array with a-priori information to compensate for spatial misalignment of the corresponding detectors in the two arrays.

In accordance with a more limited aspect of the invention, the a-priori information is determined by image data generated with a phantom.

An image artifact detecting means detects the amount of artifact related noise in selected pixels of the resultant image. An iterative correction means iteratively adjusts the registration adjustment means until the artifact related noise detected by the image pixel noise detecting means is minimized. The iterative adjustment may be along one or two axes.

In accordance with another aspect of the present invention, a method of radiographic examination is provided. Two energy radiation detector modules generate radiation attenuation signals, when aligned with the same plane, indicative of an amount of radiation impinging thereon. The radiation signals are transformed into pixel values of an image representation. At least one of the radiation signals is altered to compensate for misregistration of spatial positions of corresponding radiation detectors. For example, a fraction of the signal from each detector might be summed with a complementary fraction of the signal from an adjacent detector of the same array.

In accordance with one more limited aspect of the present invention, the two detector arrays are configured to be responsive to different energies of radiation.

In accordance with another more limited aspect of the invention, the two arrays are sequentially sampled as each shifts into alignment with the plane.

One advantage of the present invention is that it provides improved basis images.

Another advantage of the present invention is that it simplifies detector alignment.

Yet another advantage of the present invention resides in the ease with which compensation can be made for detector misalignment.

Still further advantages of the present invention will become apparent to those of ordinary skill in the art upon reading and understanding the following detailed description of the preferred embodiment.

BRIEF DESCRIPTION OF THE DRAWINGS

The present invention may take form in various components and arrangements of components and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
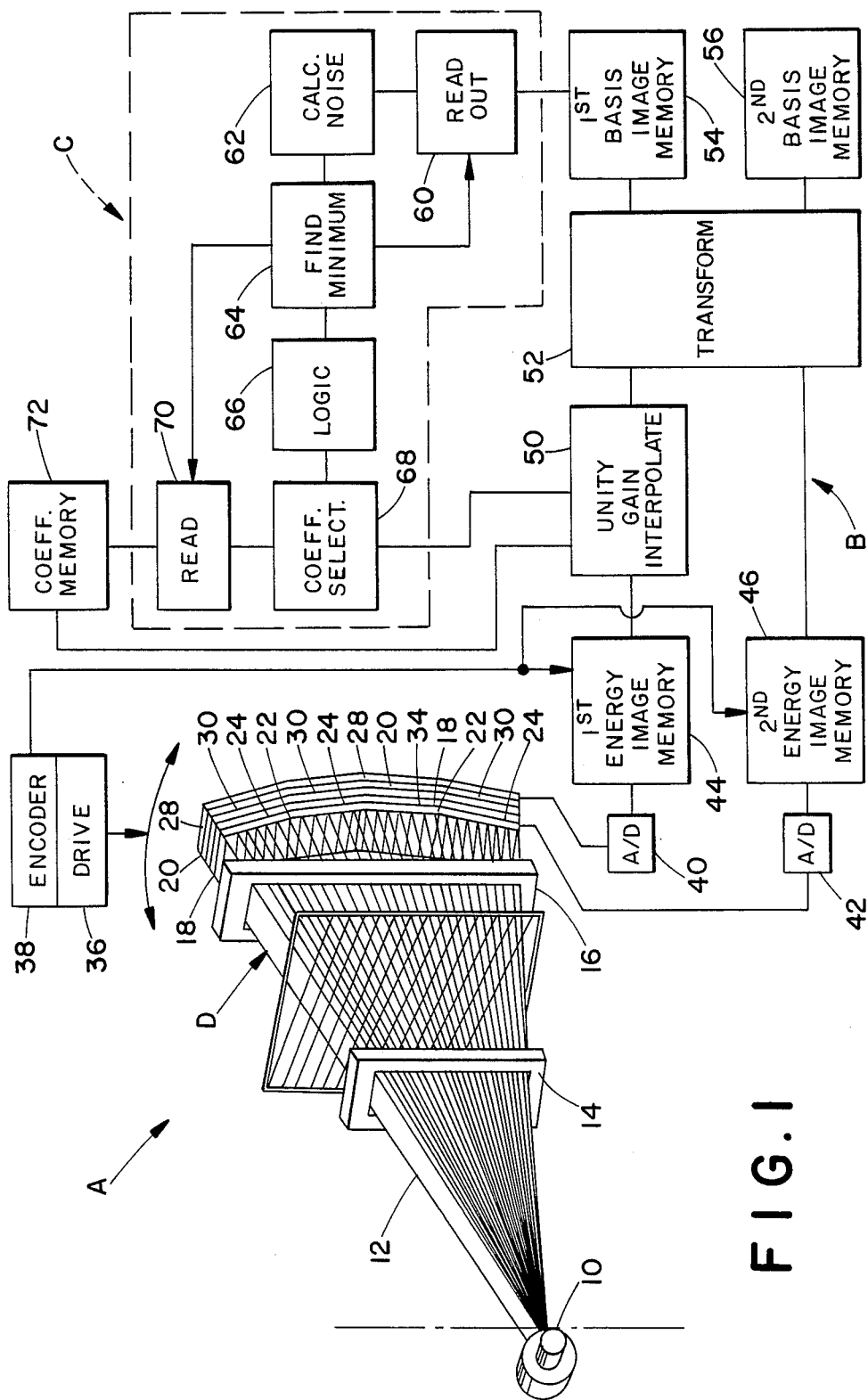
FIG. 1 is a diagrammatic illustration of a dual energy detector misalignment compensation and basis image generating system in accordance with the present invention.

With reference to FIG. 1, a radiographic scanner A transmits radiation energy through an examination region and generates radiation signals indicative of the radiation transmissivity or attenuation along each of a plurality of paths through the examination region. The radiographic scanner generates two or more radiation signals corresponding to x-ray beam attenuation or transmission through the same or generally aligned radiation paths. An imaging means B converts the radiation signals into images. In the dual energy embodiment, the images are material specific, basis images. More specifically, using known non-linear algorithms, an amount of selected material along the selected path is determined from the difference in the relative amounts of high and low energy radiation attenuated or transmitted along the selected radiation path. An iterative registration adjustment means C alters at least one of the first and second radiation signals before the algorithm operation such that each represents a more coincident path. In this manner, errors due to misregistration of the energy paths are corrected.

The radiographic scanner A includes a radiation source 10, such as an x-ray tube, which generates a polyenergic fan beam 12 of x-rays having at least two energy levels. An entrance collimator 14 and an exit collimator 16 collimate the x-ray beam passing through the examination region or region of interest to a predetermined fan shape. A first or low energy detector array 18 includes a plurality of radiation detectors for detecting the low energy x-ray photons. A second or high energy x-ray detector array 20 includes a plurality of detectors disposed behind the low energy detector array to detect the high energy x-ray photons. The first and second detector arrays are arranged along an arcuate path such that each detector is equidistant from the x-ray source. The arrays may be linear, one detector wide arrays, multilinear arrays.

Figure 2:
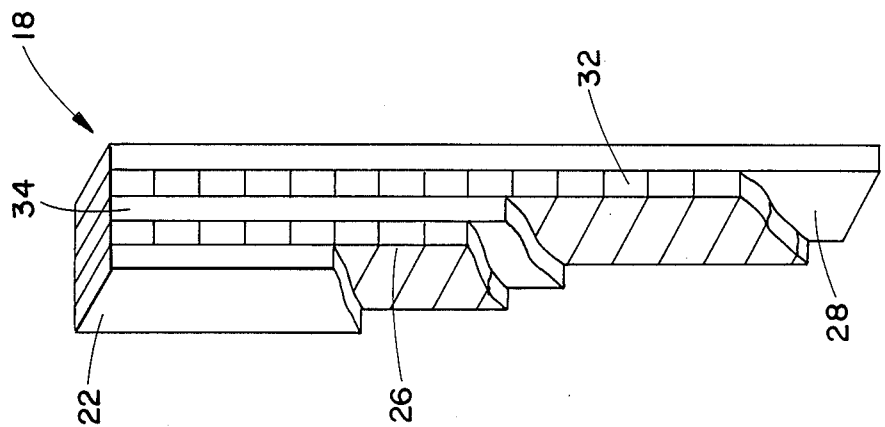
FIG. 2 is a detailed sectional view illustrating one embodiment of construction of the dual energy radiation detectors.

With particular reference to FIG. 2, a linear detector array is shown. The first detector array 18 includes a phosphor or scintillator screen 22. For manufacturing simplicity, the first detector array includes a plurality of first detector modules 24. Each detector module includes a plurality of photodiodes 26, e.g. 32 diodes per module. Each row may be one or more photodiodes wide, dependent on a particular flux density. The number of modules is selected such that when arranged end to end, the modules span the fan beam. The second detector array 20 includes a second phosphor or scintillator screen 28 to which a plurality of second detector modules 30 are mounted. Each second detector module includes a plurality of photodiodes 32. The first and second detector modules are arranged a pair. The rows are substantially in alignment with each other, the examination region and the x-ray beam. The corresponding detector columns of each module receive radiation which has traversed substantially the same plane through the image region and corresponding first and second module detectors receive radiation which has traversed generally the same one pixel square path.

The stopping power of the first scintillator screen is such that primarily low energy photons are stopped and transformed to light, while the high energy photons pass therethrough. The high energy scintillator screen is configured of a higher atomic number material with more stopping power to stop and convert the higher energy photons into light. To assure selected difference in energy between the high and low energy levels, an x-ray absorptive material 34, such as a sheet of copper, may be disposed between the first and second phosphor screens.

The copper serves to further separate high and low energy radiation photons that has sufficient energy to pass through the low energy scintillator such that only higher energy photons reach the high energy scintillator. By selecting the thickness of the copper sheet, the difference in the energy of photons detected by the high and low energy detectors is selected.

A mechanical drive 36 causes the first and second detector arrays 18, 20, the entrance collimator 14, and the exit collimator 16 to sweep transverse to the plane of the beam such that a rectangular region of interest of the patient is sequentially irradiated. An encoder 38 provides a spatial position address indicative of the spatial position to which each element of data from the detector arrays corresponds. Each time the detector arrays are swept a distance corresponding to one pixel, the address is changed. In this manner, sweeping the detector array provides analogous data to a pair of stationary rectangular detector grids that are large enough to span the entire swept area. Optionally, such a detector grid may be provided.

With the phantom D disposed in the examination region, each detector produces an analog radiation signal which varies in proportion to the intensity of x-rays traversing a corresponding path through the phantom. Analog-to-digital converters 40, 42 convert the analog radiation signals into digital representations of radiation intensity.

High and low image representations are each defined by a matrix of image pixels. The digital pixel values corresponding to each pixel are stored in corresponding memory elements of high and low energy image memories 44, 46, respectively. For a single vertical column or linear array detector, one row of pixels of each image corresponds to a common photodiode in the detector array. Each time the linear detector array is swept an incremental transverse distance, the data for the next adjacent pixel column is generated. Because the high and low energy detectors are substantially back to back, the corresponding pixel in the high energy image representation memory represents substantially the same subregion of the region of interest. However, the normal small degree of misalignment causes the corresponding high and low energy image pixels to represent slightly different regions of interest. With a multilinear detector array, each image pixel value is the sum of data as from the detectors in a horizontal row as each detector is swept across the same position.

A unity gain interpolation or other registration correction means 50 adjusts the spatial position represented by pixels in one of the image memories with a-priori information. More specifically, the interpolation means averages the digital signal from one pixel and the digital signal from a corresponding pixel in the next row with a unity gain. For example, 90% from one and 10% from the other. Because the basis transformation is non-linear, a non-unity gain can be expected to cause significant degradation in the material specific images. The weighting percentage or coefficient is indicative of the degree of misalignment of the corresponding high and low energy detectors. The lower the percentage or coefficient from the neighboring pixel, the greater the alignment between the high and low energy detectors.

A larger coefficient or percentage reflects a greater misalignment that is being corrected. For example, a 50% or half and half averaging shifts the apparent position of the given pixel to the midway point between the two detectors. A 10% contribution from the neighboring pixel shifts the apparent spatial position one tenth of the way from the center of selected pixel toward the 10% contributing pixel. By selecting the registration coefficient, the apparent spatial position between the two interpolated pixels is selectable. Optionally, other unity gain interpolations may be utilized.

A basis transform means 52 transforms corresponding pixels from the first and second image memories into corresponding pixel values for forming composite images such as first and second basis images. A particular non-linear basis transform algorithm is well known in the art and is described in Lehman, L. A.; GENERALIZED IMAGE COMBINATION IN DUAL KVP DIGITAL RADIOGRAPHY; Phys. Med. Biol., 1981, 8 659–667; the contents of which are incorporated herein by reference. The basis images are stored in first and second basis image memories 54, 56. In the preferred embodiment, the first basis image represents soft tissue and the second basis image represents calcium. Other material specific images can, of course, be generated utilizing known basis image transform algorithms.

The a-priori information on which the unity gain interpolation is based is developed in an initial calibration procedure. An iterative registration adjustment means C selectively adjusts the registration coefficients applied by the linear interpolation means 50 until artifact noise in the corresponding pixels of one of the basis images is minimized. A basis image pixel reading means 60 reads out selected pixel values from the first basis image memory means. A noise calculating means 62 determines phase change artifacts or other noise in each sampled pixel. A minimum determining or optimizing means 64 determines that determined noise is least. That is, each of a plurality of registration correction coefficients are utilized for each group of rows of pixel values used to generate the basis image. In the preferred embodiment, each module is one group of rows. Larger or smaller row groups may be selected, possibly as small as a single row. The minimum determining means determining which coefficient produces a basis image with the least artifact degradation in the corresponding row group. A logic means 66 controls the selection of coefficients for the coefficient correction means 50 by a coefficient selecting means 68. The logic control means 66 causes the coefficient selecting means 68 to select coefficients in a pattern which homes in on the minimum determined noise in an efficient manner. When the minimum or optimum is located, a read-out means 70 is actuated to cause the coefficient to be transferred to a registration correction coefficient memory 72. More specifically, the coefficient is transferred to a storage location corresponding to the photodiode pair. The determination of calibration coefficients can be simplified by assuming that all detectors in each module have the same misalignment and calculating one coefficient per module.

For a multilinear, the phantom is rotated 90° and the procedure is repeated to generate horizontal correction coefficient values for each column. In the preferred embodiment, each coefficient adjusts a module or other group of column values. The horizontal and vertical alignment procedures may be alternated to fine tune coefficients. Optionally, the groups may be larger or smaller.

Figure 3:
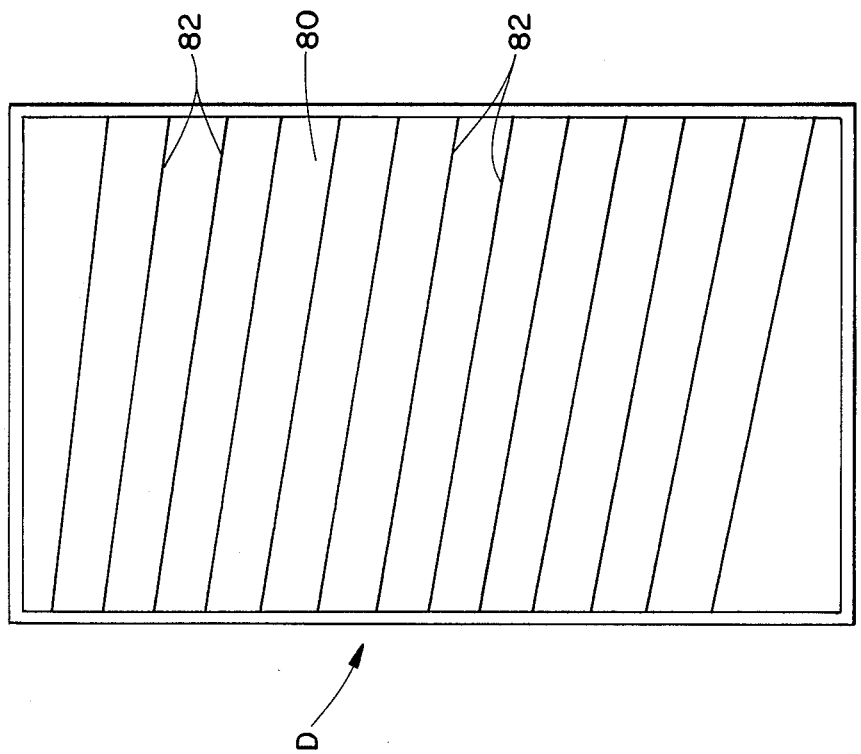
FIG. 3 is a front view of the phantom of FIG. 1.

With particular reference to FIG. 3, the phantom D includes a uniform thickness sheet 80 of a generally tissue equivalent material, e.g. plexiglass. The sheet has sufficient height to span the fan beam and a sufficient width to span the fan beam sweep. A plurality of high atomic number strips 82 extend across the phantom. Preferably, the high atomic number radiation blocking material is angled and has a diameter which is less than half the vertical height of an individual photodetector. If in a perfect registration, the wire covers one photodiode pair at a time. The transistion of the angled wire from one pair to another, if in exact registration, occurs at the same time. The most notable phase change is at the pair boundary if registration is inaccurate. In the preferred embodiment, the dense strips are a 9 mil copper wire and the detectors are 0.45 millimeters high.

The wires are mounted to an x-ray absorbtive material, such as a tissue equivalent material which brings the phantom into a normal calibration range for the scanner. The wires are angled such that as the detector array is swept, the shadow cast by each of the wires moves across about two and a half detector modules. This allows sampling of each module at a plurality of wire alignments. A sufficient number of the wires are provided such that each detector is shadowed at least once during the sweep. Preferably, sufficient wires are provided to shadow and sample each detector pair a plurality of times.

In a system which is calibrated for soft tissue and calcium, a material such as copper, which is denser than calcium, provides a small negative residual in the soft tissue image, even with perfect registration. When the high and low energy detectors are not perfectly registered, a positive artifact is present on one side of the wire and a negative artifact on the other. The greater the misregistration, the greater the positive and negative artifacts. These artifacts increase the local standard deviation of the artifact noise measured by the noise measuring means 62.

In the preferred embodiment, the phantom is positioned in the examination region and the x-ray beam is scanned thereacross. This generates a full set of pixel values for each of the high and low energy image memories 44, 46. The basis transformation means 52 performs a basis transformation on the two sets of data to generate a first, preferably soft tissue, basis image which is stored in the first basis image memory means 54. The pixel by pixel read-out means 60 reads the 32 horizontal pixel value rows of the basis image which correspond to the data collected by one of the detector modules. The noise calculating means 62 calculates the noise which in part is attributable to the phase change artifacts from the positive and negative artifacts on either side of each wire.

A registration coefficient is selected. For example, a registration coefficient could be selected which causes each pixel value of the first image memory to be replaced with a value equal to 80% of its value plus 20% of the value of the pixel directly above it. This exemplary registration adjustment shifts the effective spatial position represented by the pixels of one energy upward by one fifth of the detector height relative to the same pixels of the other energy. The basis transformation means transforms the pixel values from the first and second image memories with the registration correction to derive another basis image. The pixel read-out means 60 reads out the row of 32 pixel values for the same detector module and the noise calculating means 62 determines the noise. Because the same image data is utilized, any change in the basis image is attributable to the registration coefficient change. A reduction in the determined noise indicates that the spatial shift caused by the selected registration coefficient improves the effective registration of the corresponding pairs of detectors. This process is repeated iteratively with different registration correction coefficients until a minimum noise level is determined for each module. The registration correction coefficient which provides the minimum noise level is stored in the coefficient memory 72.

The process is then repeated for each of the detector modules and the determined registration correction coefficient is stored in memory 72. For a multilinear array, the phantom is rotated 90° and the process is repeated, module by module, to determine registration coefficients along the other axis of the array. The horizontal and vertical registration coefficients procedures may be repeated for fine tuning. Once the registration correction coefficients for a given detector array are determined, the registration coefficients are used each time a pair of basis images are generated. New coefficients normally do not need to be recalculated or determined for the life of the array. However, if the array is repaired, replaced, removed from the machine, or its position in the machine adjusted or realigned, then the iterative registration coefficient calculation procedure is repeated.

Figure 4:
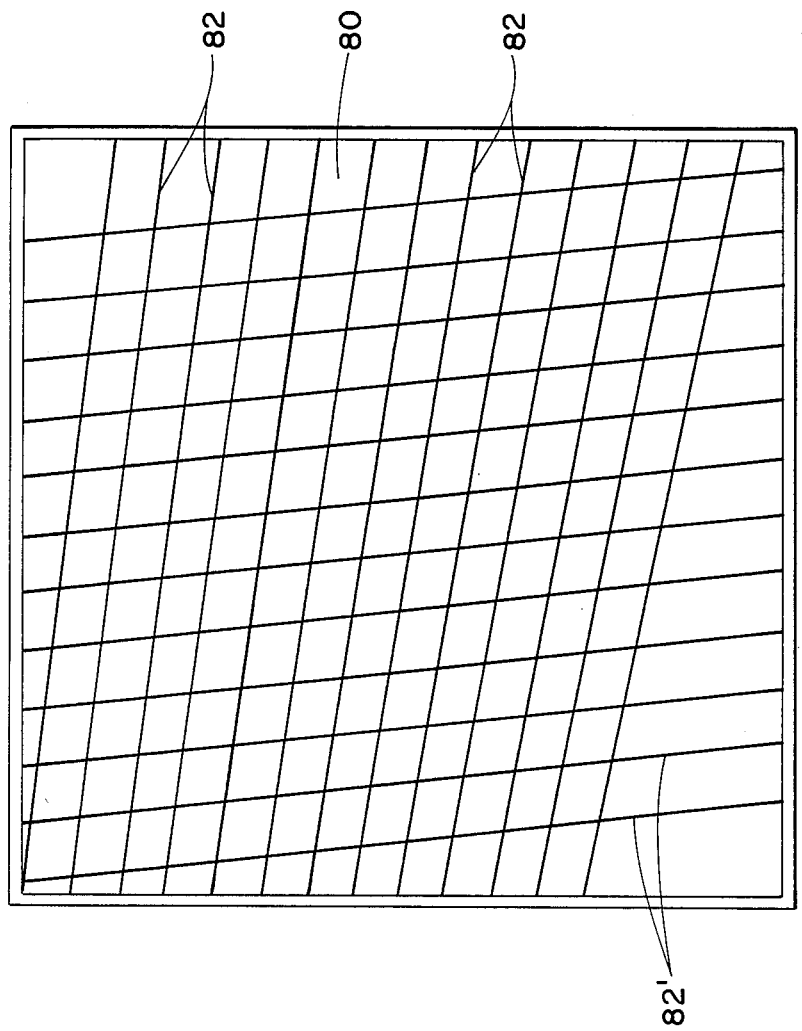
FIG. 4 is an alternative embodiment of the phantom.

With reference to FIG. 4, the phantom may be provided with a second set of wires 82'. The second wires are angled relative to an orthogonal axis such that horizontal and vertical registration data can be collected in a single scan. The registration coefficient determining means C may again determine the horizontal and vertical registration coefficients separately. Alternately, adjustments to both horizontal and vertical registration coefficients can be made in each cycle.

Although the preferred embodiment has been described with reference to dual energy detector arrays, the present invention has further application. For example, two or more arrays of detectors for the same energy range may be layered back to back. The transform performed by the transform means 52 may be a simple summing, weighted subtraction, or other combining algorithm to form other composite images other than the first and second basis images. The noise calculating means may again measure noise or may measure other image parameters, e.g. image sharpness. If more than two layers of detectors are provided, the layers may be individually aligned with any single layer.

The detectors in each layer need not be aligned with each other. For example, there may be a one-half detector off-set between layers. This shift can double resolution in the normal image. The same registration procedure may be followed. However, a half detector is subtracted (or added) to each detector position to account for the off-set. It is further to be appreciated that the detector arrays need not be back to back. For example, the arrays may be side to side.

The invention has been described with reference to the preferred embodiment. Obviously, modifications and alterations will occur to those or ordinary skill in the art upon reading and understanding the preceding detailed description of the preferred embodiments. It is intended that the invention be construed as including all such alterations and modifications insofar as they come within the scope of the appended claims or the equivalents thereof.

Having thus described the preferred embodiment, the invention is now claimed to be:

1. A radiographic apparatus comprising:
    a source of radiation for projecting a radiation beam through an examination region which receives a subject to be examined radiographically;

an array of first radiographic detectors for detecting radiation that has traversed the examination region and generating first signals indicative thereof;

an array of second radiographic detectors for detecting radiation that has traversed the examination region and generating second signals indicative thereof;

a transform means for deriving an image representation from the first and second signals, the transform means being operatively connected with the first and second detector arrays;

a registration correction means for operating on at least one of the first and second signals to correct for spatial misalignment of the first and second detector arrays, the registration correction means being operatively connected between the transform means and at least one of the first and second arrays.

2. The apparatus as set forth in claim 1 wherein the first detector array detects radiation in a first energy range, the second detector array detects radiation in a second energy range, and the transform means transforms the first and second signals into at least one material specific basis image representation which is stored in a basis image memory means.

3. The apparatus as set forth in claim 2 wherein the registration correction means includes a unity gain interpolation means which interpolates signals from adjacent detectors of one of the arrays with a unity gain.

4. The apparatus as set forth in claim 1 wherein the first and second detector arrays are parallel columns of a multilinear detector array.

5. The apparatus as set forth in claim 2 further including a registration correction memory means for storing a plurality of registration correction adjustments.

6. The apparatus as set forth in claim 1 further including first and second image memories for storing first and second images from the first and second detector arrays, the registration correction means being connected with at least one of the image memories, the transform means being operatively connected with the registration correction means and the other image memory.

7. The apparatus as set forth in claim 2 wherein the first and second detector arrays each include a plurality of detector modules, which detector modules each include a plurality of detectors.

8. The apparatus as set forth in claim 1 further including:
an image characteristic monitoring means for monitoring a characteristic of the image representation; and,
a registration correction adjustment means for adjusting the registration correction means until the monitored characteristic is optimized.

9. The apparatus as set forth in claim 8 wherein the characteristic monitoring means includes an image noise determining means and further including a minimum noise determining means for determining when the monitored noise is minimized, the registration adjustment means being connected with the minimum determining means.

10. The apparatus as set forth in claim 8 further including means for sweeping the first and second arrays transverse to the radiation beam.

11. The apparatus as set forth in claim 10 further including a phantom disposed in the examination region.

12. The apparatus as set forth in claim 11 wherein the phantom includes strips of high atomic number, radiation absorbing material which shadow on a part of each of a plurality of detectors as the detector sweeping means sweeps the detector arrays.

13. The apparatus as set forth in claim 12 further including a tissue equivalent material between the high atomic number strips.

14. A radiographic apparatus comprising:
means for projecting a fan beam of radiation along a plane;
a plurality of arrays of radiation detectors for detecting radiation and generating radiation signals indicative of the amount of radiation detected thereby, the detector arrays being disposed to detect radiation which has trasversed an at least partially common path;
a phantom disposed between the radiation source and the detector arrays, the phantom including a plurality of strips of radiation absorptive material that are narrower than a width of a detector element in the arrays, the strips extending at an oblique angle relative to the fan beam plane;
a drive means for sweeping the fan beam and detector arrays at an oblique angle relative to the phantom strips such that the strips of radiation absorptive material cast shifting shadows on a plurality of the detectors.

15. The apparatus as set forth in claim 14 wherein the strips are wires with a diameter that is less than a width of a detector element in the arrays.

16. A radiographic apparatus comprising:
means for projecting a fan beam of radiation;
a plurality of arrays of radiation detectors for detecting radiation and generating radiation signals indicative of the amount of radiation detected thereby, the detector arrays being disposed to detect radiation which has traversed an at least partially common path;
a phantom disposed between the radiation source and the detector arrays, the phantom including a plurality of strips of radiation absorptive material extending at an angle relative to the fan beam plane;
a drive means for sweeping the fan beam and detector arrays relative to the phantom such that the strips of radiation absorptive material cast shadows on a plurality of the detectors;
first and second phantom image memory means for storing first and second phantom images, the first and second phantom image memory means being operatively connected with the plurality of detectors for receiving the first and second signals therefrom;
a registration correction means operatively connected with at least the first phantom image memory means for interpolating values of adjacent pixels of the first phantom image memory;
a transform means operatively connected with the registration correction means and the second phantom image memory means for transforming the registration corrected pixel values from the first phantom image memory means and pixel values from the second phantom image memory means into at least one composite image representation; and,
a composite image memory means for storing the composite image representation.

17. The apparatus as set forth in claim 16 wherein:

the first and second arrays detect radiation with first and second energies;

the transformation means transforms the values into a first material specific image and a second material specific image; and, the strips are generally equivalent to the first material.

18. The apparatus as set forth in claim 17 wherein the strips are mounted to a layer that is generally equivalent to the second material.

19. The apparatus as set forth in claim 16 further including registration correction adjustment means operatively connected between the composite image memory means and the registration correction means for selectively adjusting the interpolation performed thereby.

20. The apparatus set forth in claim 19 wherein the adjustment means includes:

a composite image monitoring means for monitoring phase change artifacts of selected pixels of the composite image representation;

a minimum determining means for determining a minimum artifact degradation;

a registration coefficient selection means for selecting linear interpolation coefficients; and, a registration coefficient memory means for storing the registration coefficients which achieve the minimum artifact degradation.

21. A method of radiography comprising:

(a) collecting data representing generally the same spatial paths through an image region with each of at least two detector arrays;

(b) repeating step (a) for each of a plurality of spatial paths at least some of which intersect segments of radiation absorptive material such that any misalignment in the spatial paths of corresponding detectors in the at least two arrays causes phase change artifacts;

(c) interpolating data collected by corresponding detectors of the at least two arrays to bring the spatial path detected by the corresponding detectors into more precise spatial alignment;

(d) after interpolation, transforming the data from the detector arrays into at least one composite image representation.

22. The method as set forth in claim 21 further including:

(d) monitoring a portion of the composite image representation corresponding to the spatial path detected by the corresponding detectors of the at least two arrays;

(e) determining a relative level of phase artifact degradation of the monitored composite image representation portion;

(f) adjusting the interpolation until the detected phase artifact degradation is minimized; and, (g) repeating steps (c) through (g) for each of a plurality of corresponding detectors of the at least two arrays.

23. The method as set forth in claim 22 wherein:

the at least two detector arrays each detect different energies of radiation; and, the transform means transforms the data from the at least two arrays into material specific, basis image representations.

* * * * *